(12) United States Patent
Bateman (10) Patent No.: US 7,820,966 B2
(45) Date of Patent: Oct. 26, 2010

(54) MASS SPECTROMETER

(75) Inventor: Robert Harold Bateman, Cheshire (GB)

(73) Assignee: Waters Technologies Corporation, Milford, MA (US)

( * ) Notice: Subject to any disclaimer, the term of this patent is extended or adjusted under 35 U.S.C. 154(b) by 334 days.

(21) Appl. No.: 11/909,996

(22) PCT Filed: Apr. 3, 2006

(86) PCT No.: PCT/GB2006/001207

§ 371 (c)(1),
(2), (4) Date: Jun. 20, 2008

(87) PCT Pub. No.: WO2006/103465

PCT Pub. Date: Oct. 5, 2006

(65) Prior Publication Data

US 2008/0265152 A1  Oct. 30, 2008

Related U.S. Application Data

(60) Provisional application No. 60/671,364, filed on Apr. 14, 2005.

(30) Foreign Application Priority Data

Apr. 1, 2005 (GB) .................................. 0506665.9

(51) Int. Cl.
*B01D 59/44* (2006.01)
*H01J 49/00* (2006.01)

(52) U.S. Cl. .................................. 250/283; 250/281
(58) Field of Classification Search ......... 250/281–283, 250/287–289
See application file for complete search history.

(56) References Cited

U.S. PATENT DOCUMENTS

| 5,811,059 A | 9/1998 | Genovese et al. |
| 6,831,271 B1 * | 12/2004 | Guevremont et al. ....... 250/282 |
| 2002/0060288 A1 | 5/2002 | Hughey et al. |
| 2004/0136872 A1 | 7/2004 | Miller et al. |

FOREIGN PATENT DOCUMENTS

| CA | 2273322 | 2/2000 |
| WO | 97/23779 | 7/1997 |
| WO | 98/42006 | 9/1998 |
| WO | 02/071053 | 9/2002 |

* cited by examiner

*Primary Examiner*—Jack I Berman
*Assistant Examiner*—Meenakshi S Sahu
(74) *Attorney, Agent, or Firm*—Jamie H. Rose (57) ABSTRACT

A mass spectrometer is disclosed comprising a High Pressure Liquid Chromatography system (10) which is interfaced to a combustion chamber (16) and isotope ratio mass analyser (19) by means of an Electrospray Ionisation ion source (11) and a Field Asymmetric Ion Mobility Spectrometry device (13). Analyte and solvent molecules are ionised by the ion source (11). Desired analyte ions are substantially onwardly transmitted by the Field Asymmetric Ion Mobility Spectrometry device (13) to the combustion chamber (16) whereas undesired solvent ions are substantially attenuated by the Field Asymmetric Ion Mobility Spectrometry device (13).

25 Claims, 2 Drawing Sheets

FIG. 1

PRIOR ART

FIG. 2

MASS SPECTROMETER

CROSS REFERENCE TO RELATED APPLICATIONS

This application is the National Stage of International Application No. PCT/GB2006/001207, filed on Apr. 3, 2006, which claims priority to and benefit of U.S. Provisional Patent Application Ser. No. 60/671,364, filed on Apr. 14, 2005, and priority to and benefit of United Kingdom Patent Application No. 0506665, filed Apr. 1, 2005. The entire contents of these applications are incorporated herein by reference.

The present invention relates to an isotope ratio mass spectrometer and a method of isotope ratio mass spectrometry.

It is known to measure the relative abundances of specific isotopes of an element using a mass spectrometer. This field of measurement is commonly referred to as Isotope Ratio Mass Spectrometry ("IRMS").

The measurement of the isotopes of carbon which comprise an organic material may be carried out by initially combusting the organic material in a combustion chamber having an atmosphere of oxygen. This process yields carbon dioxide, water and oxides of any other elements in the organic substance. The combustion chamber may comprise a catalyst, for example copper oxide, which may be heated, for example, to approximately 900° C. The carbon dioxide is then separated from the other products of oxidation by, for example, a process of cryogenic trapping. The carbon dioxide is then passed to an isotope ratio mass spectrometer for measurement of the relative abundance of its isotopes.

A known isotope ratio mass spectrometer comprises an Electron Impact ion source, a magnetic sector mass analyser and three Faraday ion detectors. One of the ion detectors is arranged to the detect ions having a mass to charge ratio of 44, another ion detector is arranged to detect ions having a mass to charge value of 45 and a further ion detector is arranged to detect ions having a mass to charge value of 46. Measurements of the relative ion signals for these three mass to charge values allows the carbon isotope ratio $^{13}C/^{14}C$ and the oxygen isotope ratio $^{18}O/^{16}O$ to be determined. Alternatively, if the sample is known to contain the radioactive isotope of carbon ($^{14}C$) and the oxygen isotope ratio is known, then the carbon isotope ratio $^{14}C/^{12}C$ may be determined.

It is also known to use a quadrupole mass filter instead of a magnetic sector mass analyser. The quadrupole mass filter may be arranged to be switched to transmit, in sequence, ions having mass to charge values of 44, 45 and 46 onto a single ion detector.

An alternative known arrangement which is suitable for measuring the isotopes of carbon comprises an Accelerator Mass Spectrometer ("AMS"). Accelerator Mass Spectrometers are, however, relatively large and expensive.

It is known to separate the components of a mixture by gas chromatography prior to combustion to carbon dioxide. However, many substances are not easily separated by gas chromatography. Substances that cannot be separated by gas chromatography include polar molecules and thermally labile molecules. These classes of substances include a large proportion of biological molecules which are potentially of interest. This class of substances also includes the metabolite products of endogenous and xenobiotic compounds.

It is known to attempt to measure the isotopes of carbon within organic materials or analytes which have been separated by reverse phase liquid chromatography. However, this is particularly problematic due to the fact that the solvent used in reverse phase liquid chromatography is usually a variable mixture of water and an organic solvent such as methanol or acetonitrile. Accordingly, the solvent will comprise varying amounts of organic materials containing the elements carbon and hydrogen (and possibly also oxygen, nitrogen and sulphur). These will be present at concentrations which are several orders of magnitude greater than the concentration of the analyte which is desired to be measured. As a result, any attempted measurement of the isotope ratios of carbon in the analyte will be severely distorted or masked by the significantly greater abundance of carbon from the solvent.

It is known to attempt to collect fractions from a High Pressure Liquid Chromatography ("HPLC") liquid eluent. The solvent present in the fractions is then allowed to evaporate. The remaining analyte material is then combusted with oxygen to yield carbon dioxide and other oxides. However, this approach requires a relatively large number of fractions to be collected and analysed since the exact elution time of any particular analyte of interest cannot be reliably predicted. If it is not known in advance what analytes may be present in a sample and which of these analytes may need to be analysed, then a very large number of fractions may potentially need to be obtained and subsequently analysed. This approach can therefore be significantly time consuming and expensive. Furthermore, an analyte eluting may end up being split between two or more fractions and/or a fraction may contain two or more analytes. If the analyte is split between two or more fractions then the precision of isotope ratio measurement may be reduced. If a fraction contains two or more analytes then the isotope ratio may be distorted due to the presence of another component with a different isotope ratio.

At present, a practical way of interfacing a High Pressure Liquid Chromatography ("HPLC") system to a combustion region arranged upstream of an isotopic ratio mass spectrometer such that all solvents (and in particular all organic solvents) are successfully removed prior to the combustion products being passed to the isotopic ratio mass spectrometer is not known. Furthermore, an interface which allows the measurement of isotope ratios in real time is also not known. Similarly, an interface which allows the isotope ratio for carbon and other elements to be measured for each component as it elutes from an HPLC column whilst retaining chromatography resolution is also not known.

Attempts have been made to directly interface an HPLC system to an isotope ratio mass spectrometer but these have historically been restricted to HPLC separations involving aqueous solutions only. This has, however, severely restricted the range of analyte materials, and their complexity, which can be analysed.

A mechanical arrangement which attempts to directly interface an HPLC system to an Isotope Ratio Mass Spectrometer is known. In this arrangement the liquid eluent from the HPLC system is deposited on to a continuously moving wire loop. The liquid droplets attach to the wire by surface tension. The wire is then heated by passing electrical current through it thereby promoting evaporation of the solvent. The wire with desolvated analyte material is then passed directly into the combustion region. The analyte is combusted in the combustion region in an atmosphere of oxygen thereby forming carbon dioxide and other oxides. The carbon dioxide isotope ratios can then be measured.

The known arrangement is, however, particularly problematic to regulate. Reverse phase liquid chromatography typically involves using two or more solvents in ratios that vary during the course of a liquid chromatography run. Accordingly, during the liquid chromatography run the solvent composition will change and as a result the solvent surface tension and volatility will also change. The optimum liquid flow rate will therefore also change. A yet further complication is that the heating requirements will also change during the course of a liquid chromatography separation. There is a delicate balance to be maintained between on the one hand incomplete desolvation and incomplete combustion (which can lead to background contamination and memory effects) and on the other hand excessive combustion which can lead to failure of the wire loop.

It is therefore desired to provide an improved mass spectrometer.

According to an aspect of the present invention there is provided a mass spectrometer comprising:

a first device for separating or dispersing analyte atoms, molecules or ions;

a first ion source arranged downstream of the first device, the first ion source being arranged and adapted to ionise analyte atoms, molecules or ions received from the first device;

a second device for separating analyte ions from other ions, the second device comprising one or more electrodes;

a combustion chamber arranged to receive and at least partially combust at least some analyte ions; and a mass analyser arranged downstream of the combustion chamber.

The first device preferably comprises a chromatography device for separating or dispersing analyte atoms or molecules by means of chromatography. According to an embodiment the first device comprises a gas chromatography device. However, more preferably, the first device may comprise a liquid chromatography device. Alternative embodiments are also contemplated wherein the first device is selected from the group consisting of: (i) a super-critical fluid chromatography device; (ii) a capillary electrophoresis device; and (iii) a capillary electrophoresis chromatography device.

The first ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

The first ion source may comprise a pulsed or continuous ion source.

The second device is preferably selected from the group consisting of: (i) a high field asymmetric waveform ion mobility separator or spectrometer; (ii) an ion mobility separator or spectrometer; (iii) a gas phase electrophoresis device; (iv) a differential ion mobility separator, spectrometer or device; (v) a Field Asymmetric Ion Mobility Spectrometry ("FAIMS") device; (vi) a gas phase ion separator or spectrometer; (vii) a device for separating ions according to their mobility; and (viii) a device for separating ions according to differences or changes of their ion mobility with electric field strength.

The mass spectrometer preferably comprises first voltage means arranged and adapted to apply an asymmetric voltage waveform to the one or more electrodes. The asymmetric voltage waveform preferably comprises at least a first voltage component $V_{high}$ having a first peak amplitude and at least a second voltage component $V_{low}$ having a second peak amplitude, wherein the first peak amplitude is substantially different to the second peak amplitude.

The first peak amplitude is preferably positive or negative and/or the second peak amplitude is preferably positive or negative. The first peak amplitude and/or the second peak amplitude are preferably selected from the group consisting of: (i) less than −5000 V; (ii) −5000 to −4500 V; (iii) −4500 to −4000 V; (iv) −4000 to −3500 V; (v) −3500 to −3000 V; (vi) −3000 to −2900 V; (vii) −2900 to −2800 V; (viii) −2800 to −2700 V; (ix) −2700 to −2600; (x) −2600 to −2500 V; (xi) −2500 to −2400 V; (xii) −2400 to −2300 V; (xiii) −2300 to −2200 V; (xiv) −2200 to −2100 V; (xv) −2100 to −2000 V; (xvi) −2000 to −1900 V; (xvii) −1900 to −1800 V; (xviii) −1800 to −1700 V; (xix) −1700 to −1600 V; (xx) −1600 to −1500 V; (xxi) −1500 to −1400 V; (xxii) −1400 to −1300 V; (xxiii) −1300 to −1200 V; (xxiv) −1200 to −1100 V; (xxv) −1100 to −1000 V; (xxvi) −1000 to −900 V; (xxvii) −900 to −800 V; (xxviii) −800 to −700 V; (xxix) −700 to −600 V; (xxx) −600 to −500 V; (xxxi) −500 to −400 V; (xxxii) −400 to −300 V; (xxxiii) −300 to −200 V; (xxxiv) −200 to −100 V; (xxxv) −100 to 0 V; (xxxvi) 0 to 100 V; (xxxvii) 100 to 200 V; (xxxviii) 200 to 300 V; (xxxix) 300 to 400 V; (xl) 400 to 500 V; (xli) 500 to 600 V; (xlii) 600 to 700 V; (xliii) 700 to 800 V; (xliv) 800 to 900 V; (xlv) 900 to 1000 V; (xlvi) 1000 to 1100 V; (xlvii) 1100 to 1200 V; (xlviii) 1200 to 1300 V; (xlix) 1300 to 1400 V; (l) 1400 to 1500 V; (li) 1500 to 1600 V; (lii) 1600 to 1700 V; (liii) 1700 to 1800 V; (liv) 1800 to 1900 V; (lv) 1900 to 2000 V; (lvi) 2000 to 2100 V; (lvii) 2100 to 2200 V; (lviii) 2200 to 2300 V; (lix) 2300 to 2400 V; (lx) 2400 to 2500 V; (lxi) 2500 to 2600 V; (lxii) 2600 to 2700 V; (lxiii) 2700 to 2800 V; (lxiv) 2800 to 2900; (lxv) 2900 to 3000 V; (lxvi) 3000 to 3500 V; (lxvii) 3500 to 4000 V; (lxviii) 4000 to 4500 V; (lxix) 4500 to 5000 V; and (lxx) greater than 5000 V.

The first and/or second peak amplitudes are preferably with respect to the time averaged mean voltage applied to the one or more electrodes of the second device.

The first voltage component is preferably applied or is present for a first time period $T_{high}$ and the second voltage component is preferably applied or is present for a second time period $T_{low}$. The first time period $T_{high}$ is preferably shorter, longer or substantially the same as the second time period $T_{low}$. The first time period $T_{high}$ and/or the second time period $T_{low}$, are preferably selected from the group consisting of: (i) <0.1 μs; (ii) 0.1-0.5 μs; (iii) 0.5-1 μs; (iv) 1-2 μs; (v) 2-3 μs; (vi) 3-4 μs; (vii) 4-5 μs; (viii) 5-6 μs; (ix) 6-7 μs; (x) 7-8 μs; (xi) 8-9 μs; (xii) 9-10 μs; (xiii) 10-11 μs; (xiv) 11-12 μs; (xv) 12-13 μs; (xvi) 13-14 μs; (xvii) 14-15 μs; (xviii) 15-16 μs; (xix) 16-17 μs; (xx) 17-18 μs; (xxi) 18-19 μs; (xxii) 19-20 μs; and (xxiii) >20 μs.

The asymmetric voltage waveform preferably comprises a waveform selected from the group consisting of: (i) rectangular; (ii) non-rectangular; (iii) curved; (iv) regular; (v) irregular; (vi) stepped; (vii) saw-tooth; and (viii) sinusoidal.

The mass spectrometer preferably comprises second voltage means arranged and adapted to apply a DC compensation voltage to the one or more electrodes. The DC compensation voltage is preferably selected from the group consisting of: (i) less than −1000 V; (ii) −900 to −800 V; (iii) −800 to −700 V; (iv) −700 to −600 V; (v) −600 to −500 V; (vi) −500 to −400 V; (vii) −400 to −300 V; (viii) −300 to −200 V; (ix) −200 to −100 V; (x) −100 to −90 V; (xi) −90 to −80 V; (xii) −80 to −70 V;

(xiii) −70 to −60 V; (xiv) −60 to −50 V; (xv) −50 to −40 V; (xvi) −40 to −30 V; (xvii) −30 to −20 V; (xviii) −20 to −10 V; (xix) −10 to 0 V; (xx) 0 to 10 V; (xxi) 10 to 20 V; (xxii) 20 to 30 V; (xxiii) 30 to 40 V; (xiv) 40 to 50 V; (xxv) 50 to 60 V; (xxvi) 60 to 70 V; (xxvii) 70 to 80 V; (xxviii) 80 to 90 V; (xxix) 90 to 100 V; (xxx) 100 to 200 V; (xxxi) 200 to 300 V; (xxxii) 300 to 400 V; (xxxiii) 400 to 500 V; (xxxiv) 500 to 600 V; (xxxv) 600 to 700 V; (xxxvi) 700 to 800 V; (xxxvii) 800 to 900 V; (xxxviii) 900 to 1000 V; and (xxxix) more than 1000 V.

In a mode of operation the second voltage means may be arranged and adapted to sweep, vary, progressively vary or switch the DC compensation voltage applied to the one or more electrodes. The second voltage means may be arranged and adapted to sweep, vary, progressively vary or switch the DC compensation voltage in a generally or substantially stepped, linear, regular, irregular, periodic or non-periodic manner.

According to the preferred embodiment the mass spectrometer preferably further comprises means arranged so as to provide a first stream of gas which flows, in use, through the second device. Preferably, at least some ions are arranged to be onwardly transmitted axially through the second device by being entrained in the first stream of gas.

The first stream of gas may comprise one or more gases selected from the group consisting of: (i) nitrogen; (ii) helium; and (iii) oxygen.

The second device may comprise two or more substantially parallel electrodes. Alternatively, the second device may comprise two or more substantially co-axial cylindrical, spherical or hemispherical electrodes.

The second device may comprise one or more electrodes arranged substantially or generally in the plane in which ions are transmitted, in use, through the second device. The second device may comprise a plurality of axial segments or an array of electrodes. The second device may comprise, for example, at least 2, 3, 4, 5, 6, 7, 8, 9, 10, 11, 12, 13, 14, 15, 16, 17, 18, 19, 20 or more than 20 axial segments or electrodes.

The mass spectrometer may further comprise further voltage means arranged and adapted to apply one or more voltages or potentials or one or more voltage or potential waveforms to the plurality of axial segments or the array of electrodes in order to urge, propel, force or accelerate at least some ions through and/or along at least a portion of the axial length of the second device.

The further voltage means may be arranged and adapted to apply one or more transient DC voltages or potentials or one or more transient DC voltage or potential waveforms to the plurality of axial segments or the array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the second device.

The further voltage means may be arranged and adapted to apply one or more substantially constant DC voltages or potentials to the plurality of axial segments or the array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the second device.

The further voltage means may be arranged and adapted to apply two or more phase-shifted AC or RF voltages to the plurality of axial segments or the array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the second device.

According to an embodiment the mass spectrometer may further comprise means for applying a two-phase or multi-phase AC or RF voltage or signal to the one or more electrodes of the second device in order to radially confine at least some ions within the second device. The AC or RF voltage or signal preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz. The amplitude of the AC or RF voltage or signal is preferably selected from the group consisting of: (i) <50V peak to peak; (ii) 50-100V peak to peak; (iii) 100-150V peak to peak; (iv) 150-200V peak to peak; (v) 200-250V peak to peak; (vi) 250-300V peak to peak; (vii) 300-350V peak to peak; (viii) 350-400V peak to peak; (ix) 400-450V peak to peak; (x) 450-500V peak to peak; and (xi) >500V peak to peak.

The second device preferably comprises a substantially linear, non-linear, regular, non-regular or curved ion guiding region.

According to the preferred embodiment the second device comprises a Field Asymmetric Ion Mobility Spectrometry device. However, less preferred embodiments are also contemplated wherein the second device comprises an ion mobility spectrometer or separator wherein ions are separated according to their ion mobility. In such an embodiment the second device preferably comprises a drift tube. The drift tube may comprise a plurality of ring electrodes through which ions are transmitted in use. A DC only voltage gradient is preferably maintained, in use, along at least 5%, 10%, 15%, 20%, 25%, 30%, 35%, 40%, 45%, 50%, 55%, 60%, 65%, 70%, 75%, 80%, 85%, 90%, 95% or 100% of the axial length of the drift tube.

The second device is preferably maintained, in use, at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) >100 mbar; (viii) >1000 mbar; (ix) 0.0001-0.001 mbar; (x) 0.001-0.01 mbar; (xi) 0.01-0.1 mbar; (xii) 0.1-1 mbar; (xiii) 1-10 mbar; (xiv) 10-100 mbar; and (xv) 100-1000 mbar. The second device may be maintained, in use, at a pressure selected from the group consisting of: (i) <0.0001 mbar; (ii) <0.001 mbar; (iii) <0.01 mbar; (iv) <0.1 mbar; (v) <1 mbar; (vi) <10 mbar; (vii) <100 mbar; and (viii) <1000 mbar.

The second device is preferably arranged and adapted to separate analyte ions from solvent ions. The analyte ions are preferably arranged to be substantially onwardly transmitted by the second device whereas the solvent ions are preferably arranged to be substantially attenuated by the second device.

The second device may be arranged and adapted to receive a substantially continuous beam of ions and may be arranged and adapted to release or eject ions as a plurality of packets or bunches of ions.

The combustion chamber is preferably arranged and adapted to combust analyte ions in an atmosphere of oxygen. The combustion chamber preferably comprises a catalyst such as copper oxide. Carbon dioxide is preferably arranged to be formed in the combustion chamber.

The mass spectrometer may comprise means arranged so as to provide a second stream of gas which flows, in use, into the combustion chamber. Preferably, at least some atoms, molecules or ions which emerge from the second device are arranged to be entrained in the second stream of gas. The second stream of gas may comprise one or more gases selected from the group consisting of: (i) nitrogen; (ii) helium; and (iii) oxygen.

One or more cryogenic traps may be provided for separating carbon dioxide from other combustion products. The one or more cryogenic traps are preferably provided downstream of the combustion chamber and/or upstream of a second ion source.

The mass spectrometer preferably comprises a second ion source arranged and adapted to ionise one or more combustion products received from the combustion chamber or which exit from the combustion chamber. The second ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

The mass analyser preferably comprises an isotope ratio mass analyser. According to a particularly preferred embodiment the mass analyser comprises a magnetic sector mass analyser with two, three or more than three ion collectors or detectors.

According to other embodiments the mass analyser may be selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an axial acceleration Time of Flight mass analyser; (xiv) an orthogonal acceleration Time of Flight mass analyser; and (xv) an Accelerator Mass Spectrometer ("AMS").

The mass analyser is preferably arranged to mass analyse or measure the relative intensities or abundances of one, two, three or more than three isotopes of carbon dioxide, said carbon dioxide being formed by combustion of analyte ions comprising carbon in the combustion chamber.

According to an aspect of the present invention there is provided a method of mass spectrometry comprising:
separating or dispersing analyte atoms, molecules or ions in a first device;
ionising analyte atoms, molecules or ions received from the first device in an ion source, the ion source being arranged downstream of the first device;
separating analyte ions from other ions in a second device, the second device comprising one or more electrodes;
receiving and at least partially combusting at least some analyte ions in a combustion chamber; and
mass analysing or measuring ions.

The method preferably further comprises ionising at least some of the combustion products formed in the combustion chamber. The step of mass analysing or measuring ions preferably comprises mass analysing or measuring the relative intensities or abundances or one, two, three or more than three isotopes of carbon dioxide. The carbon dioxide is preferably formed by combustion of analyte ions comprising carbon in the combustion chamber.

According to another aspect of the present invention there is provided a mass spectrometer comprising:
a Field Asymmetric Ion Mobility Spectrometry device arranged to transmit certain desired analyte ions and to substantially attenuate undesired solvent ions; and
a combustion chamber arranged downstream of the Field Asymmetric Ion Mobility Spectrometry device, the combustion chamber being arranged to receive analyte ions.

According to another aspect of the present invention there is provided a mass spectrometer comprising:
a Field Asymmetric Ion Mobility Spectrometry device arranged to transmit certain desired analyte ions and to substantially attenuate undesired solvent ions; and
an isotope ratio mass analyser or isotope ratio mass spectrometer arranged downstream of the Field Asymmetric Ion Mobility Spectrometry device, the isotope ratio mass analyser or isotope ratio mass spectrometer being arranged to mass analyse or measure the relative intensities or abundances of ionised combustion products.

According to another aspect of the present invention there is provided a mass spectrometer comprising:
a liquid chromatography system;
a combustion device;
a mass analyser arranged downstream of the combustion device; and
an interface device for interfacing the liquid chromatography system to the combustion device, the interface device being arranged to at least partially separate analyte ions from solvent ions and to onwardly transmit at least some analyte ions to the combustion device whilst substantially attenuating at least some solvent ions.

The interface device preferably comprises an ion source for ionising analyte and/or solvent atoms, molecules or ions and/or a Field Asymmetric Ion Mobility Spectrometry ("FAIMS") device for separating analyte ions from solvent ions. According to a less preferred embodiment the interface device comprises an ion mobility spectrometer or separator for separating ions according to their ion mobility.

According to another aspect of the present invention there is provided a mass spectrometer comprising:
an ion mobility spectrometer or separator arranged to separate certain desired analyte ions from undesired solvent ions; and
a combustion chamber arranged downstream of said ion mobility spectrometer or separator, the combustion chamber being arranged to receive analyte ions.

According to another aspect of the present invention there is provided a mass spectrometer comprising:
an ion mobility spectrometer or separator arranged to separate certain desired analyte ions from undesired solvent ions; and
an isotope ratio mass analyser or isotope ratio mass spectrometer arranged downstream of the ion mobility spectrometer or separator, the isotope ratio mass analyser or isotope ratio mass spectrometer being arranged to mass analyse or measure the ionised combustion products.

According to the preferred embodiment a High Pressure Liquid Chromatography ("HPLC") system is interfaced to an isotope ratio mass spectrometer by means of an Electrospray Ionisation ion source and a Field Asymmetric Ion Mobility Spectrometry device.

The preferred embodiment relates to an interface between an High Pressure Liquid Chromatography ("HPLC") outlet and a combustion chamber which is preferably arranged upstream of an isotope ratio mass spectrometer. The interface preferably comprises an Electrospray ionisation probe or ion source together with a Field Asymmetric Ion Mobility Spectrometry ("FAIMS") device.

The liquid eluent from a High Pressure Liquid Chromatography system is preferably connected to an Electrospray ionisation probe such that the liquid is preferably sprayed as a series of fine electrically charged droplets. The spray may be assisted by the use of a nebulising gas. The fine droplets preferably rapidly evaporate leaving a stream of analyte ions and solvent ions. The desolvation process may be assisted by the application of a heated drying gas.

The stream of analyte ions and solvent ions are preferably arranged so as to pass through a Field Asymmetric Ion Mobility Spectrometry ("FAIMS") device. Ions are preferably separated according to their differential ion mobility as they pass through the Field Asymmetric Ion Mobility Spectrometry device. The Field Asymmetric Ion Mobility Spectrometry device is preferably tuned or arranged so as to transmit certain desired analyte ions and to preferably reject or substantially attenuate at least some or substantially all solvent or background ions. The analyte ions are then preferably passed into a combustion chamber or region where the analyte ions are preferably oxidised to carbon dioxide and other oxides. If necessary, the carbon dioxide may be separated from water and other oxides by, for example, cryogenic trapping. The carbon dioxide is then preferably passed into an isotope ratio mass spectrometer for measurement of the carbon isotope ratios.

According to the preferred embodiment components within the sample to be analysed are preferably first separated by chromatography before being transported to the first ion source for ionisation. In the preferred embodiment the means for chromatographic separation comprises a liquid chromatography device. However, according to other less preferred embodiments the means for separation may comprise a supercritical fluid chromatography device, a capillary electrophoresis device or a capillary electrophoresis chromatography device.

The liquid stream containing the substance or sample to be analysed is preferably ionised by an Electrospray Ionisation ion source ("ESI") operating at atmospheric pressure. However, according to less preferred embodiments the liquid stream may alternatively be ionised by an Atmospheric Pressure Chemical Ionisation ("APCI") ion source, an Atmospheric Pressure Photo-Ionisation ("APPI") ion source or by radiation.

The ionisation process preferably yields a stream of solvent ions and analyte ions in a gas stream at atmospheric pressure. The gas may comprise a pure gas or may comprise a mixture of gases. In a preferred embodiment the gas stream is preferably nitrogen or a mixture of nitrogen and helium. The nitrogen gas may be present as a result of using nitrogen nebulising gas in order to assist the spraying process or as a result of using a heated nitrogen drying gas to assist the desolvation process (or as a combination of both processes). Alternatively, the gas or one component of the gas may be supplied separately. Other gases or gas mixtures may be used. For example, oxygen may be added to the gas stream. The oxygen may be added prior to the analyte ions entering the combustion chamber.

According to the preferred embodiment a mixture of analyte and solvent ions are preferably passed to a Field Asymmetric Ion Mobility Spectrometry device. The mixture of ions is preferably separated according to the rate of change of ion mobility of the ions with electric field strength. Analyte ions are preferably separated from solvent ions and the Field Asymmetric Ion Mobility Spectrometry device is preferably tuned or arranged so as to transmit desired analyte ions whilst at the same time preferably substantially attenuating the onward transmission of undesired solvent or background ions. Analyte or desired ions are preferably passed from the Field Asymmetric Ion Mobility Spectrometry device into a combustion chamber wherein the analyte ions are then preferably oxidised. The resultant carbon dioxide is then preferably passed to an isotope ratio mass spectrometer for determination of isotope ratios.

The technique of Field Asymmetric Ion Mobility Spectrometry ("FAIMS") preferably enables different species of ions to be separated according to their rate of change of ion mobility with electric field strength. The technique of Field Asymmetric Ion Mobility Spectrometry enables gas-phase ions to be separated at atmospheric pressure and over a wide range of pressures and temperatures. In order for a Field Asymmetric Ion Mobility Spectrometry device to operate, a relatively high periodic electric field is preferably applied to one or more electrodes between which the analyte and solvent ions are preferably arranged to pass. The applied electric field may have a strength of up to 10,000 V/cm. The periodic electric field or applied voltage waveform is preferably asymmetric in the sense that there is preferably a significant difference between the peak positive voltage and the peak negative voltage applied to the electrodes. Either the positive or the negative voltage may be the higher.

The operating principal of the Field Asymmetric Ion Mobility Spectrometry device is based on ion mobility. An electric field is preferably used to drag ions through a gas that is preferably dense enough such that the ions rapidly reach a terminal velocity. The terminal velocity is roughly proportional to the strength of the electric field. This proportionality changes at high electric field strengths and is also compound-dependent thereby permitting the separation of ions from each other.

The rate of change of ion mobility with electric field strength is not currently thought to be necessarily related to the mobility of the ion. The change of ion mobility with electric field strength is not currently well understood and is generally considered to be unpredictable. It is possible that the dependence may be due to the susceptibility of an ion to distort in the presence of a strong electric field.

If a mixture of ions having different sizes is introduced between two metal plates, then a voltage can be applied to the plates which will create a condition wherein some species of ions will drift and hit the metal plates whereas other species of ions will remain between the plates. The separation of ions between the plates requires the application of an asymmetric voltage waveform. The asymmetric voltage waveform may, for example, comprise a square voltage waveform wherein a high positive voltage is applied for a short time and wherein a low negative voltage is applied for a relatively longer time.

If the electric field(s) which is preferably created by applying the asymmetric voltage waveform is relatively weak (e.g. if the electric field never exceeds 200 V/cm) then the ions will move back and forth or oscillate during the waveform but the ions will not be urged towards either plate. If the electric field during the high-voltage part of the waveform is above about 5000 V/cm then the application of the voltage waveform will preferably cause the ions to drift in one or the other direction towards one of the plates.

The reason why the ions will drift towards a plate is due to the fact that the mobility of an ion during the application of a relatively high strength electric field is different from the mobility of the ion during the application of a relatively low strength electric field. Since the mobility of an ion defines how fast an ion will move in an electric field, then the ion will move proportionately farther when the applied electric field has a first electric field strength compared with when the applied electric field has a second different electric field strength.

The voltage waveform which is preferably applied preferably has a relatively high frequency (e.g. >200 kHz) and the small extra distance travelled during each high-voltage period preferably results in a net drift of the ion towards one of the plates. Some ions will have an ion mobility which increases with electric field strength whilst other ions have an ion mobility which decreases with electric field strength. These ions will travel in opposite directions between the plates.

Certain ions, such as a chloride ion in nitrogen or oxygen gas are known to exhibit a very large change in ion mobility with electric field strength. During the application of an asymmetric voltage waveform a chloride ion will drift very rapidly towards a plate. In contrast, some ions such as the tetrapropylammonium ion exhibit only a very small change in ion mobility with electric field strength and may drift only relatively slowly towards one of the plates.

The net drift of an ion towards one of the metal plates can be stopped or compensated for by applying a relatively small DC voltage to one of the plates. If the DC voltage is applied with an appropriate magnitude and polarity then the ion will feel the force of this further electric field and the drift of the ion will be effectively stopped. The voltage that is applied to reverse or compensate for the net ion drift is referred to hereinafter as the compensation voltage ("CV"). The voltage necessary to compensate for the net drift of a chloride ion will be relatively high since the ion mobility of such ions increases substantially at high electric fields. On the other hand, the compensation voltage necessary to stop the drift of a tetrapropylammonium ion will be relatively small. The selection and application of an appropriate compensation voltage enables the separation of ions to be effectively controlled.

If a mixture of ions is placed between two plates or electrodes and a high voltage asymmetric waveform is applied thereto, then different species of ions will begin to migrate towards one or other of the plates at rates which are characteristic of those ions. If a compensation voltage is applied then a majority of ions will still hit one of the plates. However, ions for which the applied compensation voltage is exactly the right voltage to counteract the ion drift caused by the application of the asymmetric voltage waveform will experience zero net ion drift. This enables a single species of ions to then be separated from a mixture of ions. The species of ions which are in a balanced condition at any particular time between the plates can be selected by adjusting the compensation voltage applied to the electrodes.

A mixture of ions entrained in a gas flow can be resolved into several peaks by scanning the compensation voltage and by simultaneously detecting the ions successfully transmitted between the gap between the plates. Different species of ions will be onwardly transmitted at different characteristic compensation voltages. A spectrum of peaks observed by progressively varying or scanning the compensation voltage will be referred to hereinafter as a compensation voltage spectrum.

According to an embodiment the flat metal plates may be replaced by concentric cylindrical plates. If the polarity of the asymmetric voltage waveform is such that a specific ion species would drift to the inner cylinder in the absence of an applied compensation voltage and a compensation voltage is applied so as to repel these ions away from the inner electrode, then the compensation field will balance at a particular radial distance. If a desired ion is nearer the inner electrode then it will migrate away from the inner electrode to the radial position where the compensation field is balanced. Similarly, if a desired ion is nearer the outer electrode then it will migrate away from the outer electrode to a radial position where the compensation field is balanced. As a result desired ions are preferably focused towards a fixed radial position between the electrodes. The ions are preferably distributed around this ideal location due to diffusion, space charge ion-ion repulsion and gas turbulence/movement effects.

According to another embodiment a similar focusing effect may be obtained using concentric spheres. According to a further embodiment two concentric cylindrical electrodes may be provided which terminate in two concentric hemispherical sections at one end. This embodiment may be used to further concentrate specific ions at one end of the device.

In the preferred embodiment the ions first pass through the Field Asymmetric Ion Mobility Spectrometry device before they then pass to the combustion chamber. The Field Asymmetric Ion Mobility Spectrometry device is preferably tuned or arranged to transmit analyte ions but not solvent ions. The ability of the Field Asymmetric Ion Mobility Spectrometry device to separate analyte ions from the solvent ions can be effected by the amplitude and shape of an AC or RF voltage waveform which is preferably applied to the device, the temperature of the device, the rate of gas flow through the device, and the composition of a gas in which the ions are preferably entrained. A mixture of nitrogen and helium may preferably be used. The gas composition may be adjusted in order to optimise the separation of the analyte ions from other ions. Other gas mixtures may also be used.

The onwardly transmitted analyte ions are then preferably carried in a gas stream to a combustion chamber where the analyte ions are preferably combusted with oxygen to yield carbon dioxide, water and other oxides. The combustion chamber may comprise a catalyst, e.g. copper oxide, and may preferably be heated to approximately 900° C. The carbon dioxide may then preferably be separated from other products of oxidation by, for example, a process of cryogenic trapping. The carbon dioxide is then preferably passed to an isotope ratio mass spectrometer for measurement of the relative abundance of its isotopes.

In a preferred embodiment the isotope ratio mass analyser may comprise a magnetic sector mass analyser comprising multiple ion detectors. In a less preferred embodiment the mass analyser may comprise a quadrupole mass analyser, a Time of Flight mass analyser, an ion trap mass analyser or a Fourier Transform Ion Cyclotron Resonance (FT-ICR) mass analyser.

In another embodiment the mass spectrometer may comprise an Accelerator Mass Spectrometer ("AMS"). An Accelerator Mass Spectrometer may be used to analyse carbon dioxide directly. However, more preferably, a sample may be placed in the ion source in the form of graphite. The carbon dioxide is preferably passed through a glass graphitisation tube containing titanium hydride and zinc powder as reductants and cobalt as a catalyst. The tube is preferably heated at 500-550° C. to reduce the carbon dioxide to graphite. The graphite is then preferably bombarded with caesium vapour to form negative carbon ions. This method has a particular advantage when measuring the $^{14}C$ isotope since the $^{14}N$ negative ion is unstable. As a result the measurements are substantially unaffected by the presence of nitrogen.

Various embodiments of the present invention together with an arrangement given for illustrative purposes only will now be described, by way of example only, and with reference to the accompanying drawings in which.

Figure 1:
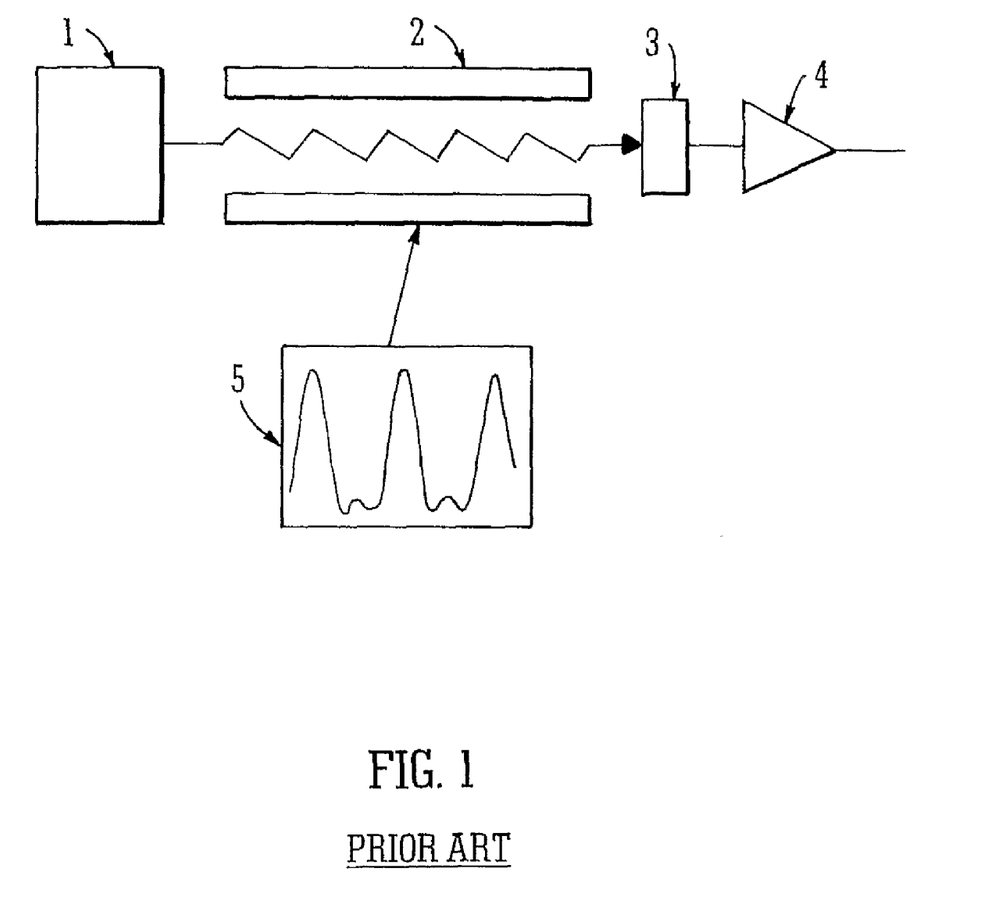
FIG. 1 shows a conventional Field Asymmetric Ion Mobility Spectrometry device.

A known Field Asymmetric Ion Mobility Spectrometry device is shown in FIG. 1. Ions are produced or generated in an ion source 1 and are then arranged so as to pass between two parallel metal electrodes 2. A flow of gas may be used in order to direct the ions so that they pass into and through the gap between the two electrodes 2. An asymmetric periodic voltage waveform 5 and a DC compensation voltage are applied to the parallel metal electrodes 2. Ions having an ion mobility that changes in a specific manner as a function of electric field strength can be arranged so as to be onwardly transmitted between the electrodes 2. However, all other ions are allowed to migrate towards one of the electrodes 2 and become lost to the system. Ions which are onwardly transmitted are detected by a plate detector 3. The ion current output from the plate detector 3 is then amplified by an amplifier 4.

Figure 2:
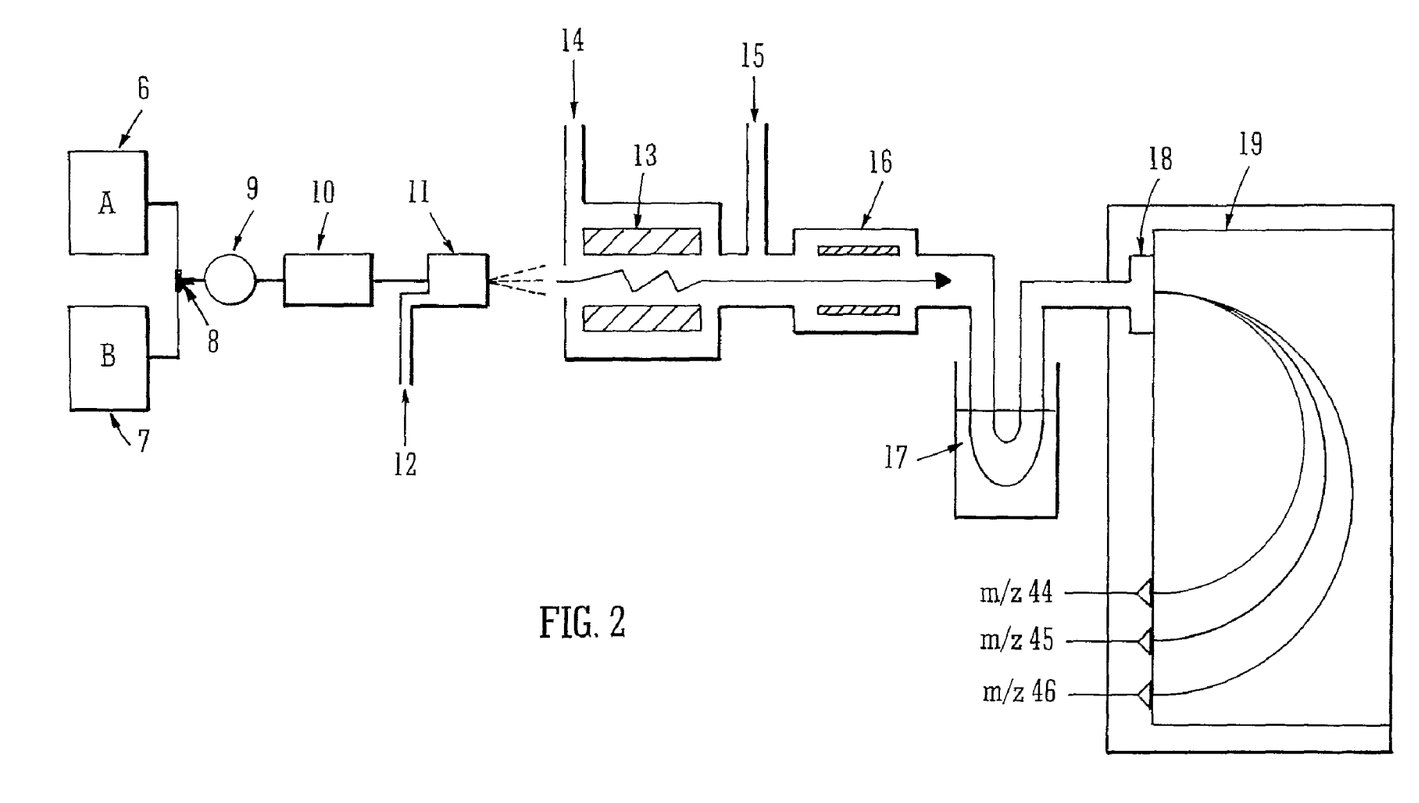
FIG. 2 shows a preferred embodiment of the present invention.

FIG. 2 shows a preferred embodiment of the present invention. The preferred embodiment preferably comprises two HPLC pumps 6,7. The HPLC pumps 6,7 are preferably arranged so as to deliver solvents A and B. One of the solvents is preferably water and the other solvent is preferably an organic solvent such as methanol. The two flows are preferably mixed in a mixing tee 8.

In normal operation the relative flow rates of the two pumps 6,7 is preferably varied whilst maintaining a substantially constant total overall flow rate. The mixture which emerges from the mixing tee 8 therefore will have variable proportions of solvent A and solvent B as a function of time. The HPLC system is therefore preferably arranged to provide a gradient flow.

The flow from the mixing tee 8 is then preferably arranged to pass through an injector 9. A sample containing an analyte mixture to be analysed is preferably injected into the liquid flow by means of the injector 9. The resulting solvent and analyte mixture is then preferably arranged to pass to a High Pressure Liquid Chromatography ("HPLC") column 10.

The solvent gradient is preferably arranged such that different components of the analyte mixture will emerge from the HPLC column 10 at different times. The analyte components which elute from the HPLC column 10 are then preferably carried or passed to an ionisation probe 11. Ions are then preferably produced or generated by Electrospray ionisation. The probe tip is preferably held at a relatively high voltage e.g. between 3 kv and 4 kV for positive ion formation and between −3 kV and −4 kV for negative ion formation. The spray may be assisted by a co-axial flow of nebulising gas. The nebulising gas may help to produce a finer spray of droplets and may also direct the droplets thereby reducing dispersion. The nebulising gas may be introduced through an inlet 12 to the probe 11. A heated drying gas may also be directed at the spray in order to assist in desolvation of the fine droplets. The desolvation gas flow is not shown in FIG. 2 for ease of illustration purposes only.

Ions which are preferably generated in the Electrospray ion source 11 are preferably desolvated and are preferably directed to pass between two parallel metal electrodes which preferably form a Field Asymmetric Ion Mobility Spectrometry ("FAIMS") device 13. However, according to an alternative embodiment the Field Asymmetric Ion Mobility Spectrometry device 13 may comprise co-axial cylindrical, spherical or hemi-spherical electrodes. A flow of gas is preferably introduced through a first gas inlet 14 to a housing which preferably encloses the Field Asymmetric Ion Mobility Spectrometry device 13. The flow of gas is preferably used to direct ions into and through the gap between the electrodes. The flow of gas may comprise helium, nitrogen or a mixture of helium and nitrogen. An asymmetric periodic voltage waveform and a DC compensation voltage are preferably applied between or to the electrodes comprising the Field Asymmetric Ion Mobility Spectrometry device 13. Ions with an ion mobility that changes in a specific way as a function of electric field strength are preferably transmitted between the electrodes. All other ions preferably migrate towards one electrode or the other and are discarded or otherwise lost to the system.

The Field Asymmetric Ion Mobility Spectrometry device 13 is preferably tuned or otherwise arranged to transmit desired analyte ions and to reject or substantially attenuate undesired solvent ions. The transmitted analyte ions are then preferably passed to a combustion chamber or region 16. Oxygen gas is preferably introduced into the combustion chamber 16 through a second gas inlet 15. The second gas inlet 15 is preferably arranged downstream of the Field Asymmetric Ion Mobility Spectrometry device 13 and/or upstream of the combustion chamber or region 16. Alternatively, oxygen gas may be introduced through the first gas inlet 14 which is preferably arranged upstream of the Field Asymmetric Ion Mobility Spectrometry device 13. The combustion chamber 16 may include a catalyst, for example copper oxide, and may be heated, for example, to approximately 900° C. The resulting carbon dioxide, water and other oxides are then preferably passed through one or more cryogenic traps 17 in which the carbon dioxide is preferably separated from the other products of oxidation. The separated carbon dioxide is then preferably submitted or passed to an isotope ratio mass spectrometer for measurement of the relative abundance of its isotopes.

In the particular embodiment shown in FIG. 2 the carbon dioxide is preferably first passed to an Electron Impact ionisation source 18 arranged upstream of a mass analyser. Carbon dioxide is preferably ionised by the Electron Impact ionisation source 18 and the resulting ions accelerated from the ion source 18 are preferably passed to a magnetic sector mass analyser 19. The ions are then preferably separated in the magnetic sector mass analyser 19. The mass analyser 19 preferably comprises three separate ion collectors for measuring the ion currents of ions having mass to charge ratios of 44, 45 and 46 respectively. Alternatively, one, two or more than three ion collectors may be provided. Other embodiments are contemplated wherein other types of mass spectrometer or mass analyser may be provided. The ratios of the three signals output from the three ion collectors are preferably used to determine the relative abundances of the isotopes of carbon. These ratios may then be compared to those of a known standard in order to minimise or eliminate instrumental factors which may otherwise distort these measurements.

Although the present invention has been described with reference to preferred embodiments, it will be understood by those skilled in the art that various changes in form an detail may be made without departing from the scope of the invention as set forth in the accompanying claims.

The invention claimed is:

1. A mass spectrometer comprising:
a first device for separating or dispersing analyte atoms, molecules or ions;
a first ion source arranged downstream of said first device, said first ion source being arranged and adapted to ionise analyte atoms, molecules or ions received from said first device;
a second device for separating analyte ions from other ions, said second device comprising one or more electrodes;
a combustion chamber arranged to receive and at least partially combust at least some analyte ions; and
a mass analyser arranged downstream of said combustion chamber.

2. A mass spectrometer as claimed in claim 1, wherein said first device comprises a liquid chromatography device.

3. A mass spectrometer as claimed in claim 1, wherein said first ion source is selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

4. A mass spectrometer as claimed in claim 1, wherein said second device is selected from the group consisting of: (i) a high field asymmetric waveform ion mobility separator or spectrometer; (ii) an ion mobility separator or spectrometer; (iii) a gas phase electrophoresis device; (iv) a differential ion mobility separator, spectrometer or device; (v) a Field Asymmetric Ion Mobility Spectrometry ("FAIMS") device; (vi) a gas phase ion separator or spectrometer; (vii) a device for separating ions according to their mobility; and (viii) a device for separating ions according to differences or changes of their ion mobility with electric field strength.

5. A mass spectrometer as claimed in claim 1, further comprising first voltage means arranged and adapted to apply an asymmetric voltage waveform to said one or more electrodes.

6. A mass spectrometer as claimed in claim 1, further comprising second voltage means arranged and adapted to apply a DC compensation voltage to said one or more electrodes.

7. A mass spectrometer as claimed in claim 1, further comprising means arranged so as to provide a first stream of gas which flows, in use, through said second device and wherein at least some ions are arranged to be onwardly transmitted axially through said second device by being entrained in said first stream of gas, wherein said first stream of gas comprises one or more gases selected from the group consisting of: (i) nitrogen; (ii) helium; and (iii) oxygen.

8. A mass spectrometer as claimed in claim 1, wherein said second device comprises two or more substantially parallel electrodes or two or more substantially co-axial cylindrical, spherical or hemi-spherical electrodes.

9. A mass spectrometer as claimed in claim 1, wherein said second device comprises a plurality of axial segments or an array of electrodes.

10. A mass spectrometer as claimed in claim 9, further comprising further voltage means arranged and adapted to apply one or more voltages or potentials or one or more voltage or potential waveforms to said plurality of axial segments or said array of electrodes in order to urge, propel, force or accelerate at least some ions through and/or along at least a portion of the axial length of said second device.

11. A mass spectrometer as claimed in claim 1, further comprising means for applying a two-phase or multi-phase AC or RF voltage or signal to said one or more electrodes of said second device in order to radially confine at least some ions within said second device.

12. A mass spectrometer as claimed in claim 1, wherein said second device is arranged and adapted to separate analyte ions from solvent ions by arranging for analyte ions to be substantially onwardly transmitted by said second device and/or for solvent ions to be substantially attenuated by said second device.

13. A mass spectrometer as claimed in claim 1, wherein said combustion chamber is arranged and adapted to combust analyte ions in an atmosphere of oxygen.

14. A mass spectrometer as claimed in claim 13, wherein said combustion chamber comprises a copper oxide catalyst.

15. A mass spectrometer as claimed in claim 1, further comprising means arranged so as to provide a second stream of gas which flows, in use, into said combustion chamber and wherein at least some atoms, molecules or ions which emerge from said second device are arranged to be entrained in said second stream of gas, wherein said second stream of gas comprises one or more gases selected from the group consisting of: (i) nitrogen; (ii) helium; and (iii) oxygen.

16. A mass spectrometer as claimed in claim 1, further comprising one or more cryogenic traps for separating carbon dioxide from other combustion products.

17. A mass spectrometer as claimed in claim 1, further comprising a second ion source arranged and adapted to ionise one or more combustion products received from said combustion chamber or which exit from said combustion chamber, wherein said second ion source is selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

18. A mass spectrometer as claimed in claim 1, wherein said mass analyser is selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an axial acceleration Time of Flight mass analyser; (xiv) an orthogonal acceleration Time of Flight mass analyser; and (xv) an Accelerator Mass Spectrometer ("AMS").

19. A mass spectrometer as claimed in claim 1, wherein said mass analyser is arranged to mass analyse or measure the relative intensities or abundances of one, two, three or more than three isotopes of carbon dioxide, said carbon dioxide being formed by combustion of analyte ions comprising carbon in said combustion chamber.

20. A method of mass spectrometry comprising:
separating or dispersing analyte atoms or molecules in a first device;
ionising analyte atoms or molecules received from said first device in an ion source, said ion source being arranged downstream of said first device;
separating analyte ions from other ions in a second device, said second device comprising one or more electrodes;
receiving and at least partially combusting at least some analyte ions in a combustion chamber; and
mass analysing or measuring ions.

21. A method as claimed in claim 20, further comprising ionising at least some of the combustion products formed in said combustion chamber and wherein the step of mass analysing or measuring ions comprises mass analysing or measuring the relative intensities or abundances of one, two, three or more than three isotopes of carbon dioxide, said carbon dioxide being formed by combustion of analyte ions comprising carbon in said combustion chamber.

22. A mass spectrometer comprising:
a liquid chromatography system;
a combustion device;
a mass analyser arranged downstream of said combustion device; and
an interface device for interfacing said liquid chromatography system to said combustion device, said interface device being arranged to at least partially separate analyte ions from solvent ions and to onwardly transmit at least some analyte ions to said combustion device whilst substantially attenuating at least some solvent ions.

23. A mass spectrometer as claimed in claim 22, wherein said interface device comprises an ion source for ionising analyte and/or solvent atoms, molecules or ions and/or a Field Asymmetric Ion Mobility Spectrometry ("FAIMS") device for separating analyte ions from solvent ions or an ion mobility spectrometer or separator for separating ions according to their ion mobility.

24. A mass spectrometer comprising:
an ion mobility spectrometer or separator arranged to separate certain desired analyte ions from undesired solvent ions; and
a combustion chamber arranged downstream of said ion mobility spectrometer or separator, said combustion chamber being arranged to receive analyte ions.

25. A mass spectrometer comprising:
an ion mobility spectrometer or separator arranged to separate certain desired analyte ions from undesired solvent ions; and
a combustion chamber arranged downstream of said ion mobility spectrometer or separator, said combustion chamber being arranged to receive analyte ions; and
an isotope ratio mass analyser or isotope ratio mass spectrometer arranged downstream of the said ion mobility spectrometer or separator, said the isotope ratio mass analyser or isotope ratio mass spectrometer being arranged to mass analyse or measure the separated analyte ions.

* * * * *